(12) United States Patent
Brisson et al.

(10) Patent No.: US 6,872,871 B2
(45) Date of Patent: Mar. 29, 2005

(54) MAPPING MOLECULAR INTERACTIONS IN PLANTS WITH PROTEIN FRAGMENTS COMPLEMENTATION ASSAYS

(75) Inventors: Normand Brisson, Montreal (CA); Stephen William Watson Michnick, Westmount (CA)

(73) Assignee: Odyssey Thera Inc., San Ramon, CA (US)

( * ) Notice: Subject to any disclaimer, the term of this patent is extended or adjusted under 35 U.S.C. 154(b) by 0 days.

(21) Appl. No.: 09/851,084

(22) Filed: May 9, 2001

(65) Prior Publication Data

US 2001/0047526 A1 Nov. 29, 2001

Related U.S. Application Data

(63) Continuation-in-part of application No. 09/017,412, filed on Feb. 2, 1998, now Pat. No. 6,270,964.
(60) Provisional application No. 60/203,937, filed on May 12, 2000.

(51) Int. Cl.[7] .............................................. C12N 15/82
(52) U.S. Cl. ....................................... 800/288; 435/468
(58) Field of Search ................................. 435/468, 419; 800/288, 278

(56) References Cited

U.S. PATENT DOCUMENTS 5,610,042 A * 3/1997 Chang et al. ............ 435/172.3
6,392,119 B1 * 5/2002 Gutterson et al. .......... 800/278

OTHER PUBLICATIONS

Florack et al. Expression of giant silkmoth cecropin B genes in tobacco. Transgenic Research, 1995, vol. 4, pp. 132–141.*
Michnick et al. Detection of protein–protein interactions by protein fragment complementation strategies. 2000, Methods in Enzymology, vol. 328, pp. 208–230.*
Pelletier et al. Oligomerization domain–dircetd reassembly of active dihydrofolate reductase from rationally designed fragments Oct. 1998, Proc. Natl. Acad. Sci. USA, vol. 95, pp. 12141–12146.*
Remy et al. Erythropoietin receptor activation by a ligand--induced comformation change. Feb. 1999, Science, vol. 283, pp. 990–993.*

* cited by examiner

Primary Examiner—Amy J. Nelson
Assistant Examiner—Cynthia Collins
(74) Attorney, Agent, or Firm—Isaac A. Angres

(57) ABSTRACT

Protein Fragment Complementation Assays (PCA) are done in plant material using enzyme fragment constructs, for example, dihydrofolate reductase (DHFR) fragment constructs. Plant material is transformed with at least two different constructs that form different products capable of interacting to reconstitute enzymatic activity in the plant material. Detection of the activity can be done using a substrate for the enzyme in the culture medium which, when reacted with the enzyme, is converted to a detectable product. One embodiment uses a substrate that can be enzymatically converted to a detectable fluorescent product. An inducer such as rapamycin or salicylic acid can be added to the culture medium to increase the level of detectable product.

1 Claim, 10 Drawing Sheets

Figure 2: Application of the DHFR PCA to the Rapamycin-induced interaction of FKBP with FRB. A, Rapamycin dose-dependent survival of CHO cells grown in nucleotide-free medium. B, Fluorescence DHFR PCA: rapamycin induces an increase in population mean fluorescence. C, Quantitative dose-response based on FACS results and D, competitive inhibition by FK506.

MAPPING MOLECULAR INTERACTIONS IN PLANTS WITH PROTEIN FRAGMENTS COMPLEMENTATION ASSAYS

This application is a continuation-in-part of U.S. Ser. No. 09/017,412 filed Feb. 2, 1998, now U.S. Pat. No. 6,270,964 granted Aug. 7, 2001, the contents of which are incorporated by reference herein, and this application also claims the benefit of U.S. provisional application No. 60/203,937 filed May 12, 2000.

BACKGROUND OF THE INVENTION

Much of modern biological research is concerned with identifying proteins involved in cellular processes and determining how, when, and where they are involved in specific biochemical pathways. However, despite recent advances in genome projects, the function of the majority of newly discovered genes remains unknown. There is now the pressing need to determine the functions of these novel gene products, such as those involved in disease phenotypes in humans or contributing to important agricultural traits in crop plants. The sequencing of the first genome of a higher plant, Arabidopsis, is now completed and sequencing programs for other plant genomes, such as rice, are in progress. These genomics programs will generate a wealth of information that is likely to offer new insights into important processes in plants and lead to exciting biotechnological applications in agriculture. However, it is in addressing questions of function where genomics-based research in plants and other organisms becomes bogged down and there is now the need for advances in the development of simple and automatable functional assays. Although many proteins have been identified by functional cloning of novel genes, such 'expression cloning' remains a significant experimental challenge. Many ingenious strategies have been devised to simultaneously screen cDNA libraries in the context of assays that allow both selection of clones and validation of their biological relevance.[1-4] However, in the absence of an obvious functional assay that can be combined with cDNA library screening, researchers have turned to strategies that use as readout some general functional properties of proteins. A first step in defining the function of a novel gene is to determine its interactions with other gene products in an appropriate context; that is, since proteins make specific interactions with other proteins as part of functional assemblies, an appropriate way to examine the function of the product of a novel gene is to determine its physical relationships with the products of other genes. This is the basis, in part, of the highly successful Yeast Two-Hybrid system.[5,6] The success of this strategy in identifying biologically significant protein-protein interactions has been well documented, whether between two specific partners or between a "bait" and "prey" library.[7,8]

The central problem with two-hybrid screening is that detection of protein-protein interactions occurs in a fixed context, the nucleus of *S. cerevisiae*, and the results of a screening must therefore be further validated as biologically relevant using other assays in appropriate cell, tissue or organism models. While this would be true for any screening strategy, it would be advantageous if one could combine cDNA library screening with tests for biological relevance into a single strategy, thus eliminating false-positive interactions immediately. It was with this goal that a general strategy for detecting protein-protein interactions in intact cells based on Protein fragment Complementation Assays (PCA) was developed (11, 13, 14). In this strategy, the gene for an enzyme is rationally dissected into two pieces. Fusion proteins are constructed with two proteins that are thought to bind to each other, fused to either of the two probe fragments. Folding of the probe protein from its fragments is catalyzed by the binding of the test proteins to each other, and is detected as reconstitution of enzyme activity. The most advanced of these PCAs is one based on murine dihydrofolate reductase (mDHFR) (see FIG. 1 and discussion below).

There are several special features of the PCA strategy that makes it an interesting alternative to the Yeast Two-Hybrid approach: 1) PCA is "complete"; no other cellular activity is necessary and as a result a PCA can be done in any prokaryotic or eukaryotic cell type, or the PCA can be directed to a specific cellular compartment, organelle or membrane surface with the inclusion of appropriate signal sequences. 2) The portability of PCAs also means that induced versus constitutive protein-protein interactions can be distinguished by doing the PCA in a cell type where specific protein-protein interactions are thought to be induced by, for example a specific signal transduction pathway. 3) PCAs are not a single assay but a series of assays. The PCA strategy therefore has the added flexibility that an assay can be chosen because it works in a specific cell type appropriate for studying interactions of some class of proteins. 4) PCAs are inexpensive, requiring no specialized reagents beyond those necessary for a particular assay and off the shelf materials and technology. 5) PCAs can be automated and high-throughput screening could be done with little human intervention. 6) PCAs are designed at the level of the atomic structure of the enzymes used; because of this, there is additional flexibility in designing the probe fragments to control the sensitivity and stringencies of the assays. 7) PCAs can be based on enzymes for which the detection of protein-protein interactions can be determined differently.[9] The simplest and most general approach is based on dominant selection, in which the reconstituted enzyme complements some missing metabolic enzyme in cells grown under selective pressure. Enzymes can also be chosen that produce a fluorescent or colored product for a more direct detection of protein-protein interactions. We have already developed 5 PCAs based on dominant-selection, colorimetric, or fluorescent outputs. Here we discuss the most well developed PCA, based on the enzyme murine dihydrofolate reductase (mDHFR) and its application to plants.[10-14] We present results demonstrating the applicability of the DHFR to study molecular interactions in plant cells, allowing the detection of constitutive and induced protein-protein interactions, different methodologies that will be applicable to broad applications in agriculture and the screening of cDNA libraries for protein-protein interactions.

The DHFR PCA was the first we developed and is the most advanced in refinement and application[12]. The instant application describes in some detail the design principles and experimental strategy of the DHFR PCA as a selection strategy in *E. coli*, with particular emphasis on necessary controls to assure that the PCA detects protein-protein interactions and not some non-specific response of living cells to expression of the enzyme fragments. A number of mutants are studied as well as detailed kinetic studies of one of the reconstituted mutant enzymes. It also describes three specific examples of protein assembly that illustrate general uses of the assay strategy. The simplest example presented is detection of GCN4 leucine zipper forming sequences, followed by the more complex interaction of the p21 ras oncogene GTPase with its downstream signaling partner, the serine/threonine kinase raf. Finally, we demonstrate a natural product-mediated protein-protein interaction, that of the ternary complex of FKBP-rapamycin with the target of rapamycin FRB.

Applicants' have had considerable success in demonstrating the use of the DHFR PCA to rapidly screen and select for optimal leucine zipper-forming sequences in a two dimensional library by library screen; the first such example in the literature.[10] These studies illustrate how the DHFR survival assay in E. coli is used to screen two libraries of complementary designed leucine zipper forming sequences each containing $10^5$ clones, resulting in $10^{10}$ potential interacting pairs of which we could practically cover $10^6$. The implications of these results are that not only does the selection strategy rapidly select for optimal properties of interacting sequences along with critical stereo- and regiospecific requirements for such complexes, but also for optimal in vivo characteristics, such as solubility and stability to proteolysis. The simplicity of this approach and specific nature of the information obtained about the design strategy suggest broad utility of the DHFR PCA in protein design and directed evolution experiments. It also shows that PCA rivals "phage display" strategies, since the entire selection, optimization and stringency tests are done in vivo, making this approach easily executed in almost any laboratory context. Most interesting are that given the sizes of the artificial libraries that we screened, by comparison, cDNA library screening with significant coverage would be feasible (for example, for libraries containing $10^3$ to $10^5$ unique cDNAs).

Recently, applicants have successfully demonstrated two different types of DHFR PCAs in mammalian cells[13,14] and fortuitously, were able to apply them to a fundamental problem in growth factor membrane receptor biology.[13] In one of these assays, the 'DHFR PCA Survival Assay', CHO DUKX-B11 (DHFR⁻) cells were co-transfected with DHFR complementary fragments F[1,2] or F[3] (FIG. 1, left) fused to two partner proteins. Co-transfectants were selected for survival in nucleotide-free medium (selection for DHFR activity). The assay has been demonstrated with GCN4 leucine zippers, the ras-raf complex, FKBP-rapamycin-FRB and the Erythropoietin (Epo) receptor and Epo Receptor-JAK2 kinase complexes.

In the second assay, the 'DHFR fluorescence PCA', the high-affinity fluorescein-conjugated DHFR inhibitor methotrexate (fMTX) passively diffuses into cells where it binds in a 1:1 complex with DHFR. Free fluorecein-methotrexate is actively transported from the cells leaving only DHFR-bound fMTX. In the DHFR PCA (FIG. 1, right), two proteins are fused to one of the two complementary fragments of DHFR (F[1,2] or F[3]) and coexpressed in a cell. If the two proteins interact, the DHFR fragments are brought into proximity and can fold/reassemble, rendering them capable of binding to fMTX. fMTX is retained in the cells and can be detected by fluorescence microscopy or fluorescence-activated flow cytometry. The first test system for the mammalian DHFR PCA was the pharmacologically well characterized rapamycin-induced association of FK506 binding protein (FKBP) to its target the FKBP-rapamycin binding domain of FRAP (FRB).[16] The DHFR-negative CHO DUKX-B11 cells were stably co-transfected with FRB and FKBP fused to one of the two DHFR complementary fragments (FRB-F[1,2] and FKBP-F[3]). Co-transfectants were selected for survival in nucleotide-free medium (selection for DHFR activity) and in the presence of rapamycin. Only cells grown in the presence of rapamycin underwent normal cell division and colony formation (FIG. 2A). Survival was dependent only on the number of molecules of DHFR reassembled, and we determined that this number is approximately 25 molecules of DHFR per cell.[14]

Formation of the FKBP-rapamycin-FRB complex was also detected in stably and transiently transfected cells with the fluorescence assay described above, based on stoichiometric binding of fluorescein-methotrexate to reconstituted DHFR in vivo. Fluorescence microscopy of unfixed co-transfected cells that had been incubated with fMTX showed high levels of fluorescence when cells were treated with rapamycin at saturating concentrations[14]. The fluorescence response of cell populations was quantified by FACS (FIG. 2B). The rapamycin-induced formation of FKBP/FRB was monitored by the shift in mean cell population fluorescence compared to non-induced cells. Quantitative rapamycin dose-dependence of this complex was demonstrated to be consistent with the known pharmacological response (FIGS. 2C, D). We have also used this approach to test a hypothesis for cytokine receptor activation suggested by the recent determination of the structure of native, unligated Epo receptor in the lab of Ian Wilson.[13, 15]

OBJECTS OF THE INVENTION

A primary object of the present invention is to develop a PCA strategy to study interactions in plant cells.

Another object of the present invention is the use of PCA for the detection of protein-protein interactions in vivo in plant cells.

A further object of the invention is the use of PCA for the detection of protein-protein interactions in appropriate contexts, such as within a specific species, organ, cell type, cellular compartment, or organelle.

Still another object of the invention is the use of PCA for the detection of induced-versus constitutive protein-protein interactions such as by environmental factors (light, cold, draught, pest and pathogens, etc.), developmental or hormonal signals.

An additional object of the invention is the use of PCA for the detection of the kinetic and equilibrium aspects of protein assembly in plant cells.

A still further object of the invention is the use of PCA for screening of cDNA libraries for protein-protein interactions.

SUMMARY OF THE INVENTION

Figure 1:
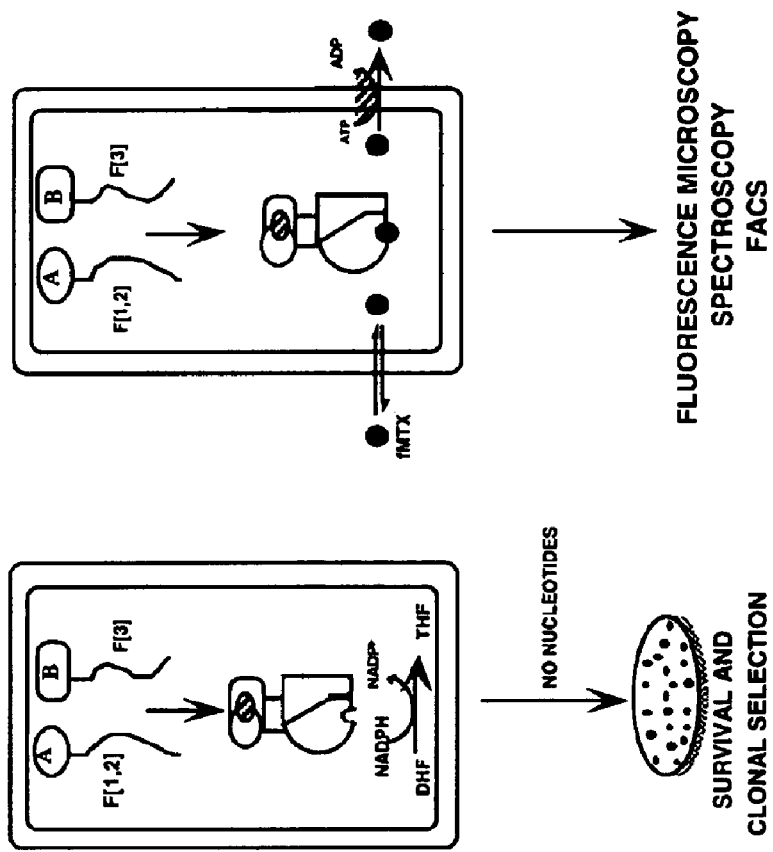
FIG. 1 illustrates a schematic representation of the strategy used to study protein-protein interactions in mammalian cells with the DHFR PCA.
Figure 2:
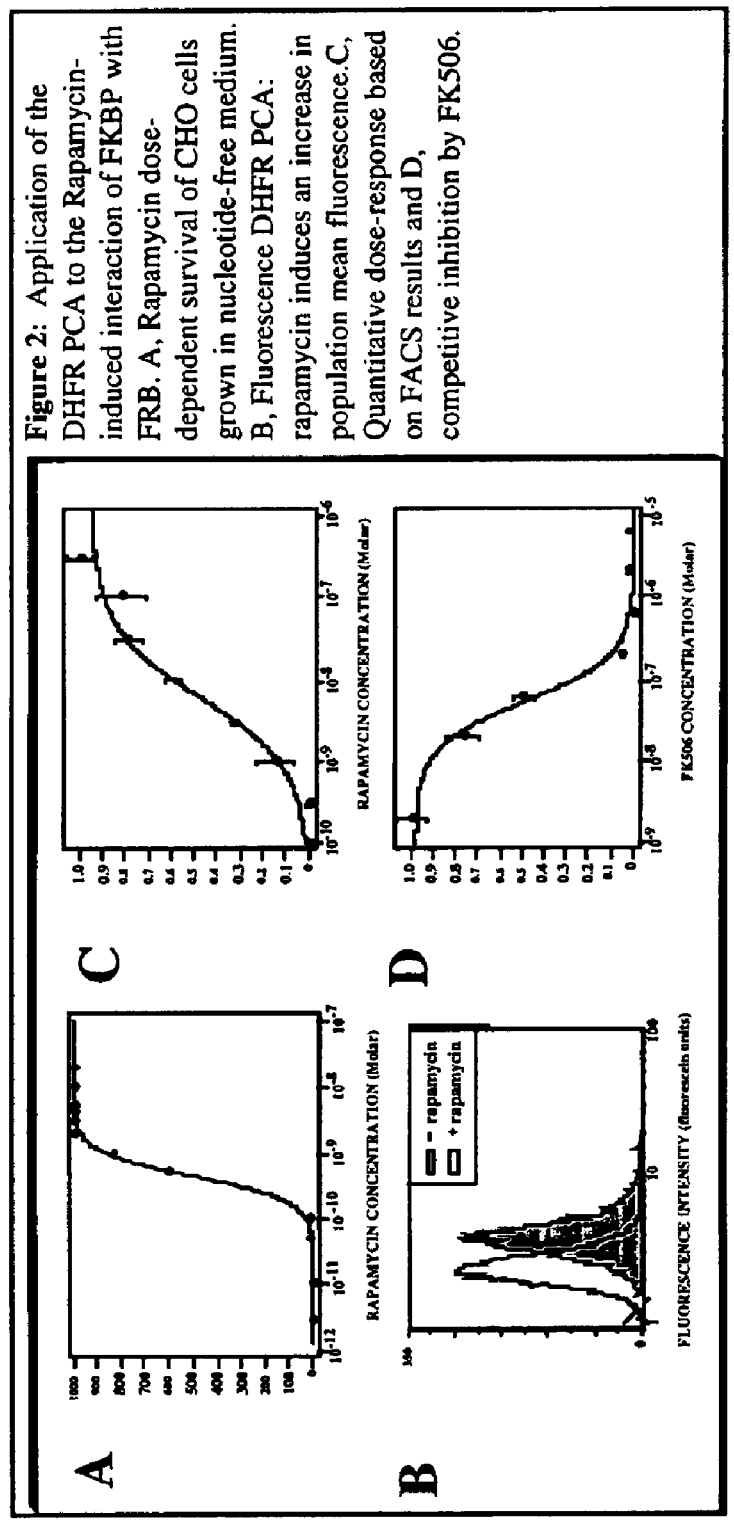
FIG. 2 shows the application of the DHFR PCA to the Rapamycin-induced interaction of FKBP with FRB.

The instant invention is directed to a method of expressing PCA interacting partners in plant material comprising: (A) transforming said plant material with: (1) a first construct coding for a first fusion product comprising (a) a first fragment of a first molecule whose fragments can exhibit a detectable activity when associated and (b) a first protein-protein interacting domain; and (2) a second construct coding for a second fusion product comprising (a) a second fragment of said first molecule and (b) a second protein-protein interacting domain that can bind (1)(b) and (B) culturing said material under conditions allowing expression of said PCA interacting partners, and (C) detecting said activity.

The present invention is also directed to a system for use as a standard or control in a PCA assay or for use in validating a PCA assay comprising: (a) a first fusion product comprising a fragment of a first molecule whose fragments can exhibit a detectable activity when associated and a first protein-protein interacting domain; and (b) a second fusion product comprising a second fragment of said first molecule and a second protein-protein interaction domain that interacts with said first protein-protein interaction domain.

The invention is also directed to a plant transgenic for one or more genes, each independently selected from the group consisting of: (A) 1 or more genes coding for 1 or more interacting partners able to participate in a PCA assay, and (B) 1 more more genes which result, either directly or indirectly, in the presence of 1 or more interacting partners able to participate in a PCA assay.

The invention also relates to a method of determining whether a mutated gene acts upstream in a pathway affecting a constitutive or inducible interaction comprising performing a PCA assay in a mutated plant and correlating a change in PCA activity, relative to that measured in a non-mutated control plant, with the presence of one or more genes acting upstream in said pathway.

The instant invention further describes a method of identifying 1 or more genes involved in a pathway controlling an inducible interaction which results in a monitorable activity comprising: (1) mutagenizing a seed from a transgenic plant expressing an interacting partner involved in PCA, (2) germinating the seed, (3) treating with an inducer that controls the interaction of any interacting partners present, and (4) monitoring said activity, and (5) correlating said acitivity with 1 or more genes involved in a pathway controlling an inducible interaction.

The invention also describes a method comprising mutating a plant or plant material that exhibits a first level of interaction between PCA interacting partners and selecting for a resultant plant or plant material that exhibits a lower level of said interaction.

The invention further describes a method of identifying plant molecule that functions as a PCA interacting partner in a PCA assay comprising: (1) reacting (A) a library of plant molecules which are fused to a first fragment of a reporter molecule, said first fragment exhibiting low or no activity, with (B) a bait molecule fused to a second fragment of said reporter molecule, said second fragment also exhibiting low or no activity and (2) correlating reconstitution of reporter molecule activity with the presence of a PCA interacting partner.

DESCRIPTION OF THE PREFERRED EMBODIMENTS

The present invention describes the use of PCA to detect protein-protein interactions in plants as well as the DHFR PCA strategy in plant protoplasts with examples of extension to broad applications in plant and agricultural problems. The invention includes the development of a system to detect inducible and non-inducible protein-protein interactions in plant cells. The development of such a system would be useful to determine whether two proteins interact together and to characterize the structural requirements for this interaction (e.g. protein domains and specific amino acids), especially in the case where the interaction is observed only under inducible conditions. The instant invention describes three approaches and the realization of the first of these approaches: 1) a transient expression approach in protoplasts; 2) transient expression in tissue explants and, 3) expression in transgenic plants.

In another embodiment, applicants' have developed a cDNA screening strategy for the identification of novel interacting proteins. This would be particularly useful to identify proteins that interact only in specific organelles or compartments or when the interaction is part of a biochemical pathway specific to plants.

The PCA strategy can be conducted on plant material selected from the group consisting of whole plants and plant-derived organs, tissues, cells, subcellular parts, and protoplasts. The plant material may also be derived from a transgenic plant.

In carrying the PCA strategy, an inducer is added to facilitate the interaction of the protein-protein interaction domains. Also in conducting the PCA of the invention, a fluorescent substrate is added and said activity is detected using fluorescence microscopy, spectrofluorometry, FACS analysis, or a fluorescence-detecting video system.

The invention also provides a system for use as a standard or control in a PCA assay or for use in validating a PCA assay comprising: (a) a first fusion product comprising a fragment of a first molecule whose fragments can exhibit a detectable activity when associated and a first protein-protein interacting domain; and (b) a second fusion product comprising a second fragment of said first molecule and a second protein-protein interaction domain that interacts with said first protein-protein interaction domain. The first and second protein-protein interaction domains are selected from the group consisting of: 1) NPR1+TGA2, 2) FKBP+FRB, 3) and leucine zippers.

The invention also describes a plant transgenic for one or more genes, each independently selected from the group consisting of: (A) 1 or more genes coding for 1 or more interacting partners able to participate in a PCA assay, and (B) 1 or more genes which result, either directly or indirectly, in the presence of 1 or more interacting partners able to participate in a PCA assay. The transgenic plant is selected form the group consisting of the genus Arabidopsis and more specifically the plant is Arabidopsis thaliana. The interacting partners comprise one or more of a leucine zipper/reporter molecule fusion, a NPR1/reporter molecule fusion, a TGA2/reporter molecule fusion, a FKBP/reporter molecule fusion or a FRB/reporter molecule fusion.

The instant invention also provides a method for determining whether a mutated gene acts upstream in a pathway affecting an interaction comprising performing a PCA assay in a mutated plant and correlating a change in PCA activity, relative to that measured in a non-mutated control plant, with the presence of one or more genes acting upstream in said pathway.

In a further embodiment, the invention directed to a method of identifying one or more genes involved in a pathway controlling an interaction which results in a monitorable activity comprising: (1) mutagenizing a seed from a transgenic plant expressing an interacting partner involved in PCA, (2) germinating the seed,- (3) treating with an inducer that controls the interaction of any interacting partners present, and (4) monitoring said activity, and (5) correlating said activity with one or more genes involved in a pathway controlling an interaction. This method could be used for cloning a gene and making products therefrom.

In another embodiment, the invention involves a method comprising mutating a plant or plant material that exhibits a first level of interaction between PCA interacting partners and selecting for a resultant plant or plant material that exhibits a lower level of said interaction.

The instant invention also provides a method of identifying a plant molecule that functions as a PCA interacting partner in a PCA assay comprising: (1) reacting (A) a library of plant molecules which are fused to a first fragment of a reporter molecule, said first fragment exhibiting low or no activity, with (B) a bait molecule fused to a second fragment of said reporter molecule, said second fragment also exhibiting low or no activity and (2) correlating reconstitution of reporter molecule activity with the presence of a PCA interacting partner.

The invention is carried out by the following but not limiting Examples.

EXAMPLES

Example 1

DNA Constructs: Genes were expressed in plant protoplasts under the control of a promoter containing two Cauliflower Mosaic Virus (CaMV) 35S enhancer elements. A plasmid containing this promoter was derived from the vector pBI221 (Clontech) by replacing the single 35S enhancer element of this vector by the double 35S enhancer element (tandem repeat of the single 35S element) of plasmid pBIN35S (gift of Dr. Daniel Matton, Université de Montréal). The resulting vector, called pBI223D, was used to construct all the plasmids required for the PCA. Sequences of the GCN4 leucine zipper-forming sequences fused to the mDHFR fragments F[1,2: Phe31Ser] and F[3] were isolated from plasmids pMT3[14] and inserted as Not1 and Xba1 fragments in pBI223D. FRB-F[1,2: Phe31Ser] and FKBP-F[3] fragments were isolated from plasmids pMT3 as Not1 and Xba1 fragments in pBI223D. DNA clones for *Arabidopsis thaliana* NPR-1 and TGA2 were obtained from Dr. Pierre Fobert, Plant Biotechnology Institute, Saskatoon and inserts amplified by PCR with appropriate linkers and cloned as N-terminal fusion to mDHFR fragments F[1,2: Phe31Ser] and F[3], respectively. The NPR1 mutant npr1-1[17] was created by using the ExSite PCR-based site directed mutagenesis kit (Stratagene) and cloned as a N-terminal fusion to mDHFR fragment F[1,2: Phe31Ser].

Example 2

Protoplasts isolation and electroporation: Leaf mesophyll protoplasts were isolated from 6-week-old in vitro grown potato plants cv. Kennebec or *Nicotiana tabacum* cv. Xanthi. The protoplast isolation procedure and culture media are as described, except for the enzymatic solution which contained 0.8% w/v cellulysin and 0.1% w/v macerase.[18,19] Electroporation of protoplasts was conducted with a homemade capacitor discharge system, using the disposable electroporation chambers (0.4 cm) of the Cell-Porator System of Gibco-BRL (Gaithersburg, Md.). The electrical pulse was delivered from a 1000 $\mu$F capacitor charged at 125 V. Pulses from the electroporator were delivered to 320 $\mu$l of protoplasts ($6 \times 10^5$ protoplasts/ml) to which was added 80 $\mu$l of a solution containing 20 mM HEPES, 300 mM NaCl, 10 mM $CaCl_2$, 770 mM mannitol and 15 ug CsCl purified supercoiled plasmid DNA for each of the DHFR fusion constructs, plus 10 ug of the plasmid pBI221. This plasmid contains the *E. coli* uidA gene, encoding the $\beta$-glucuronidase (GUS) enzyme, under the control of the CaMV 35S promoter and is used to correct for variations in electroporation efficiency.

Example 3

DHFR PCA: Following electroporation, the protoplasts were left on ice for 10 min and then transferred to petri dishes containing 3.5 ml of culture media supplemented with 50 uM 3,4-dehydro L-proline (DHP). A 1 ml aliquot was set aside for measuring GUS activity.[20] The rest of the protoplasts were centrifuged 10 min at 1500 g and resuspended in 1 ml culture media containing 50 uM DHP and 10 uM fluorescein-methotrexate (Molecular Probes). When present, rapamycin was added at a 10 nM final concentration. Salicylic acid (SA) was added at concentrations varying from 0 to 500 uM. Protoplasts were incubated at room temperature for 18 h in the dark and harvested by centrifugation as above. They were resuspended in 1 ml culture medium, collected again by centrifugation and washed twice at 37° C. for 30 min in the same culture medium containing, when required, rapamycin or SA at the appropriate concentrations. Protoplasts were then washed once in 100 mM sodium phosphate buffer (pH 7.5) containing 8% mannitol.

Example 4

Spectrofluorometer measurements: Protoplasts were lysed in 600 uL of 100 mM sodium phosphate buffer (pH 7.9) for 30 min in the dark. The lysed cells were centrifuged at 16,000 g at room temperature for 10 min. Aliquots (150 uL) were transferred into 96 well Microfluor Microtiter plates (Dynex Technologies) for fluorimeter reading using a Packard Fluorocount fluorimeter (excitation at 485 nm and emission at 530 nm). All readings were corrected for protein concentration and GUS activity.

Example 5

Flow Cytometric Analysis (FACS): Salicylic acid-induced interaction of NPR-TGA interaction in tobacco protoplasts was monitored by fluorescence flow cytometry. Histograms are based on analysis of fluorescence intensity for 10,000 cells at flow rates of 500–1000 events per second. Data were collected on a FACSCaliber (Becton-Dickinson) FACS analyzer with stimulation with an argon tuned to 488 nM with emission recorded through a 530±15 nM band width filter. Preparation of protoplasts for analysis was the same as described in DHFR PCA section. The protoplasts were incubated in 125 uM SA and the final wash of the protoplasts were done in W5 media (154 mM NaCl, 125 mM calcium chloride, 5 mM KCl, 5 mM glucose, pH 7.9). The protoplasts were then resuspended in 600 uL of W5 media for analysis.

Example 6

Fluorescence microscopy: Preparation of protoplasts for fluorescence microscopy was the same as described for FACS analysis. Additionally, protoplasts were incubated in DAPI (4,6-diamidino-2-phenylindole) nucleic acid stain at a final concentration of 1 ug/mL for 30 mins. The protoplasts were washed once with W5 media and subjected to microscopy. Microscopy was performed with a Zeiss Axioskop fluorescent microscope equipped with a 63X Plan Apochromat objective and selective filters.

Example 7

Experimental Results

Figure 3:
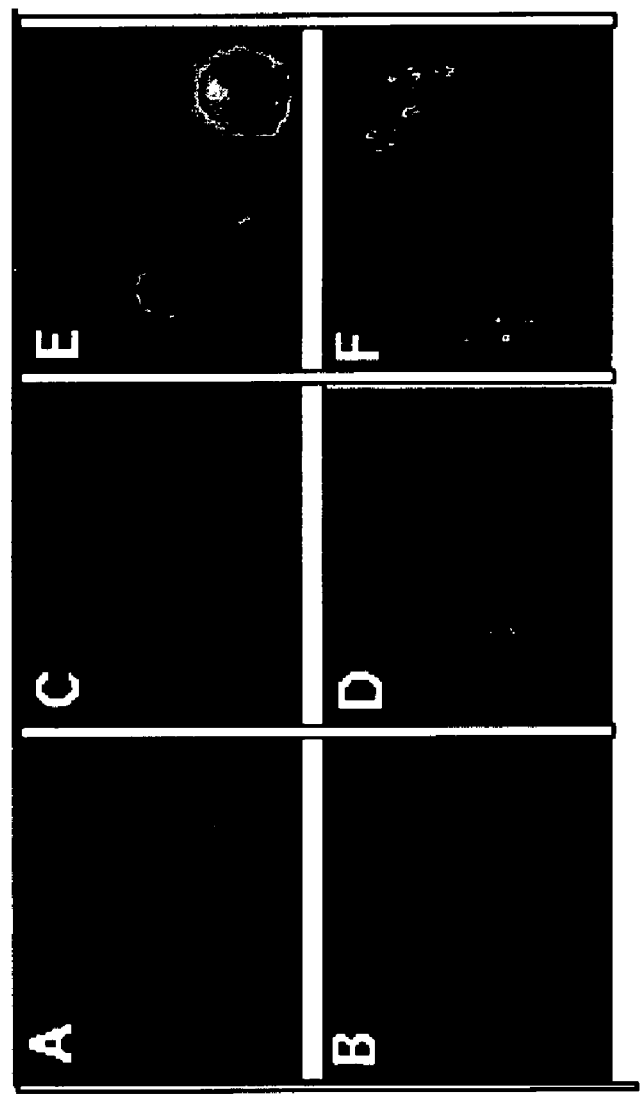
FIG. 3 describes DHFR PCA in potato protoplast.

A) Detection of inducible and non-inducible protein-protein interactions in plant cells 1) In a preliminary step in the development of a plant PCA, we have sought to reproduce in plant cells the results obtained in E. coli and animal cells with the PCA consisting of the mDHFR fragments fused to GCN4 leucine zipper forming sequences as interacting partners.[10, 11, 14] Fragments encoding the two fusion proteins were placed downstream of the strong cauliflower mosaic virus (CaMV) 35S promoter and upstream of the nopaline synthase gene terminator region in plasmid pBI222. The two recombinant plasmids were introduced singly or in combination in potato leaf protoplasts by electroporation[19]. After 20 hrs of cultivation in the presence of fMTX, protoplasts were washed with the culture medium and DHFR activity was monitored by fluorescence microscopy. Only protoplasts electroporated with the two complementary mDHFR constructs showed significant levels of fluorescence (FIG. 3). Approximately 60% of these protoplasts showed very high levels of fluorescence. The rest showed intermediate fluorescence intensities. These results indicate that plant cells can be used to monitor constitutive interactions between proteins.

Figure 4:
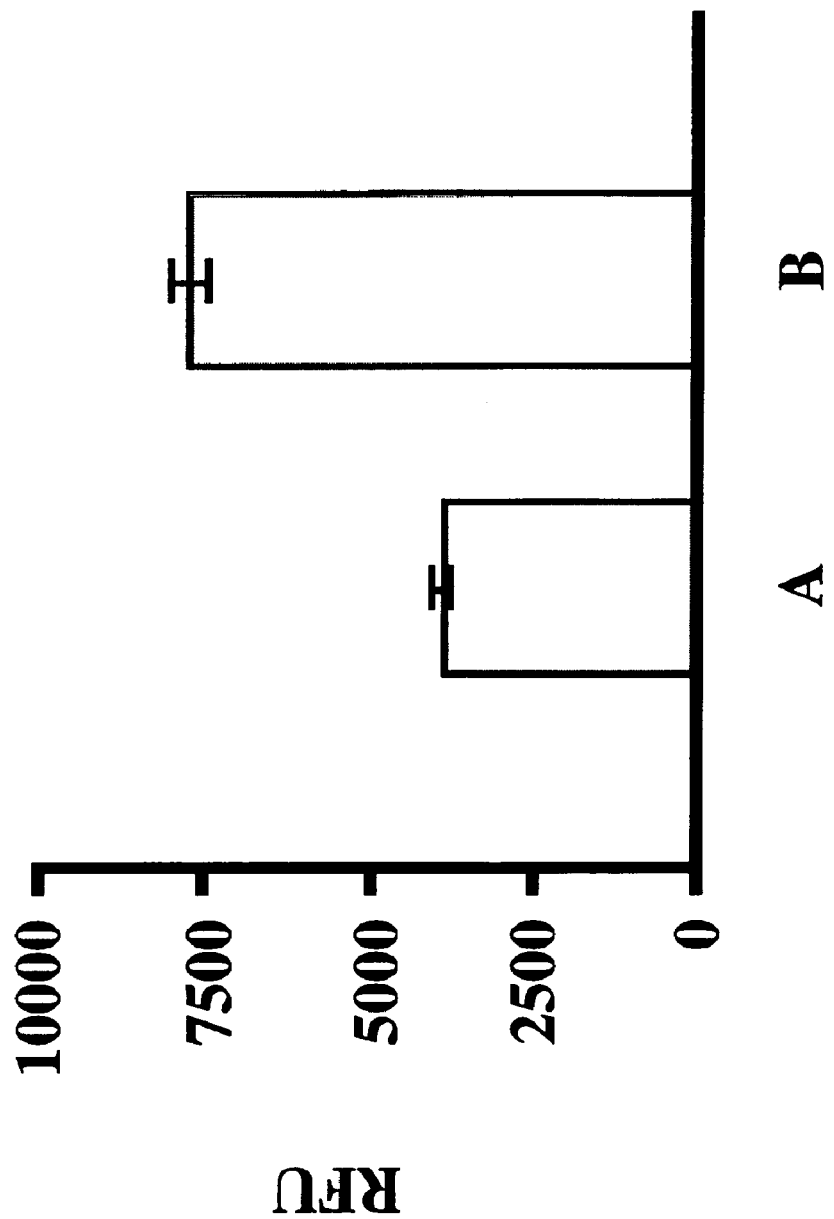
FIG. 4 shows the constitutive interaction of GCN4 leucine zippers.

Quantitative results for detection of the interaction between transiently expressed GCN4-DHFR fragments in protoplasts were obtained using a fluorescence plate reader. FIG. 4 shows that a 2.2 fold increase in fluorescence is detected in potato protoplasts transfected with the two recombinant plasmids as compared to protoplasts transformed only with the GCN4-F[1,2] plasmid. This increase in fluorescence reflects the constitutive interaction between the two GCN4 leucine zipper-forming sequences. In the experimental results illustrated in FIG. 4, potato protoplasts were electroporated with a single GCN4-F[1,2] fusion gene (A) and GCN4 leucine zipper-F[1,2] and F[3] fusions (B). The fluorometric readings obtained were subtracted from the reading obtained from the protoplasts electroporated with carrier single-stranded salmon sperm DNA. The relative fluorescence units (RFU) have been adjusted to both protein and GUS values. These results are representative of at least three independent experiments performed in triplicates.

2) Interactions controlled by a ligand: Applicants' have extended the application of the DHFR PCA in plants to inducible interactions, specifically an interaction triggered by ligand binding. These types of interactions are particularly important as they are implicated in the control of nearly all signal transduction pathways in eukaryotes. As an example, we have used the rapamycin induced association of FKBP to FRB described above, to test for the possibility of measuring ligand-induced protein interactions in plants. We used the same experimental approach as that described above for the GCN4 leucine zippers. The GCN4-DHFR fusion proteins were replaced by the same fusion proteins used in the experiments in CHO cells[14] (see above).

Following coelectroporation of tobacco leaf protoplasts with the FKBP and FRB DHFR plasmids (see Methods), the fluorescence response of cell populations in the presence or absence of rapamycin was quantified by fluorimetry. In the Experiment illustrated in FIG. 5, Rapamycin was added to tobacco leaf protoplasts electroporated with either FRB-F[1,2: Phe31Ser] or the combined FRB-F[1,2: Phe31Ser] and FKBP-F[3] constructs. The fluorometric readings obtained from cells transformed with the single plasmid were subtracted from the readings obtained from the protoplasts transformed with the combined plasmids. These relative fluorescence units (RFU) have been adjusted to both protein and GUS values. This is representative of at least two independent experiments and performed in triplicates.

Figure 5:
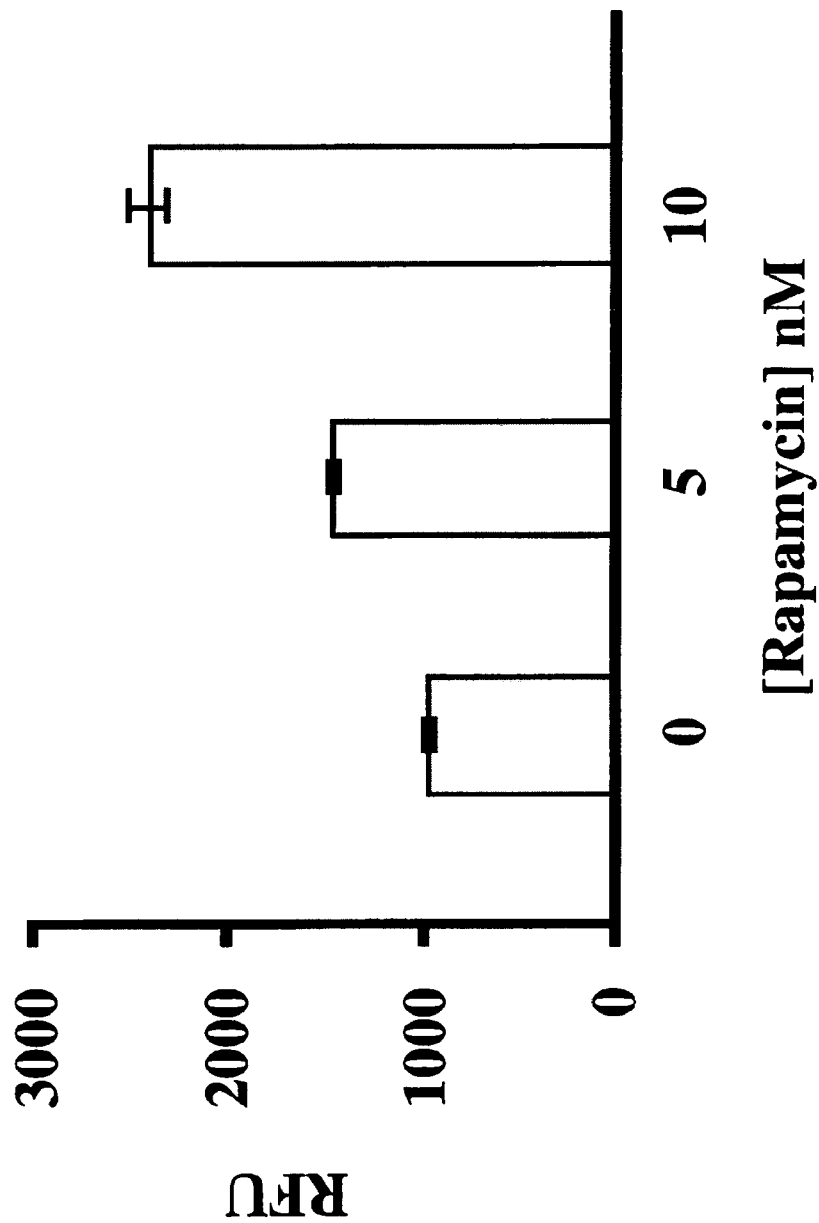
FIG. 5 illustrates how Rapamycin induces the interaction between FKBP and FRB in plant cells.

FIG. 5 shows a 1.5 and 2.3 fold increase in fluorescence when the transfected cells are incubated in the presence of 5 nM or 10 nM of rapamycin, respectively. These results indicate that the induced-interaction of foreign proteins can be monitored in plant cells using the PCA.

3) Interaction between NPR1 and TGA2: In plants, systemic acquired resistance (SAR) is a general disease resistance response that can be induced during attempted infection by an avirulent pathogen. SAR induction is mediated by salicylic acid (SA), which stimulates the expression of a number of defense-related genes, including the pathogenesis-related (pr) genes.[23] Using pr genes as reporters, a class of Arabidopsis thaliana mutants have been identified which is impaired in the SA-induced pr gene expression. All mutants in this class are mutated at the same locus, npr1 (also known as nim1).[17, 24] npr1 mutants fail to express a number of pr genes and show enhanced susceptibility to infection, even after treatment with SA. Recently, yeast two-hybrid screens have shown that tomato and Arabidopsis npr1 interacts with TGA bZIP transcription factors, some of which have been shown to bind to sequence elements in the promoter of pr genes.[25, 26, 27]

Figure 6:
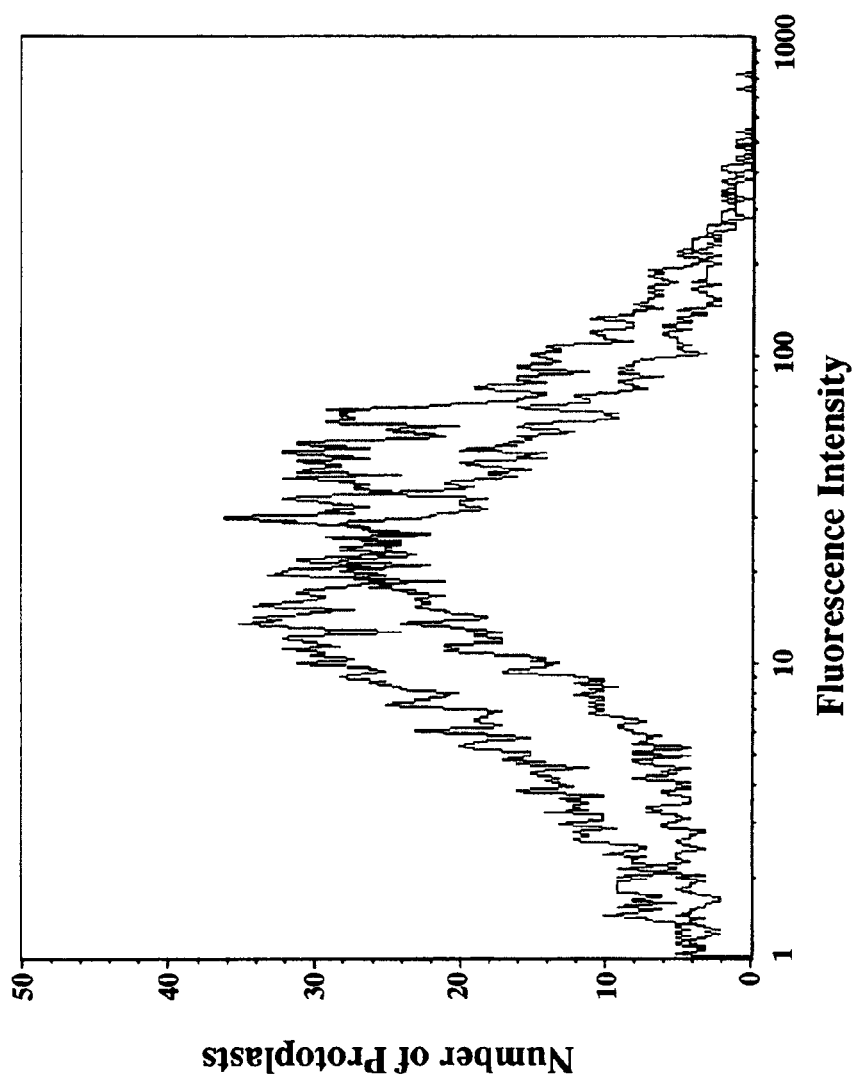
FIG. 6 describes the flow cytometric analysis of the induced interaction between NPR1 and TGA2.

Applicants' have also used the PCA system to demonstrate that NPR1 and the bZIP transcription factor TGA2 interact in planta and that this interaction is under the control of SA. We have expressed Arabidopsis NPR1 and the TGA2 bZIP transcription factor as fusion proteins with the mDHFR fragments and test whether SA can induce the interaction between these two proteins, and thus the PCA response. The NPR1 and TGA2 genes were obtained from Dr. Pierre Fobert of The Plant Biotechnology Institute, Saskatoon. DHFR activity was measured after electroporation of the constructs into tobacco or potato leaf protoplasts. Following coelectroporation of the protoplasts with the NPR1 and TGA2 DHFR plasmids (see Methods), the fluorescence response of cell populations in the presence or absence of SA was first quantified by FACS. The SA-induced formation of NPR1/TGA2 was monitored by the shift in mean cell population fluorescence compared with non-induced cells (FIG. 6). This shift corresponds to a 4-fold increase of fluorescence in the cells population. The histogram at the right (green) corresponds to cells expressing NPR1-F[1,2] and TGA2-F[3] and that have been treated with 125 uM SA. The histogram at the left (purple) corresponds to cells transfected with the same plasmids but untreated.

Figure 7:
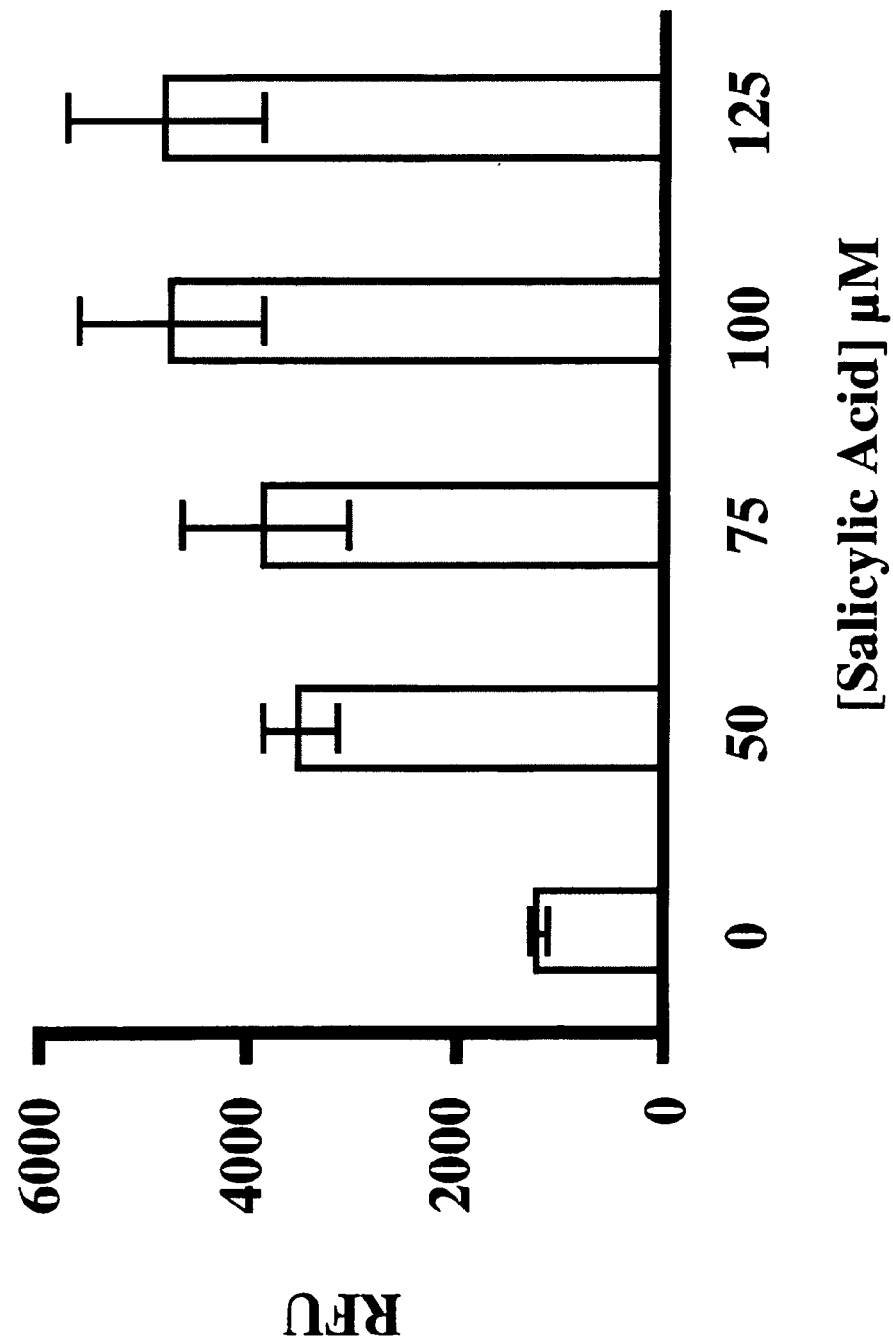
FIG. 7 illustrates the dose-response of NPR1-TGA2 in tobacco leaf protoplasts treated with SA.

FIG. 7 shows a dose-response histogram for SA with tobacco cells based on fluorescence measurements with the fluorimeter. A low level of fluorescence is detected in the absence of SA, reflecting some constitutive interaction between NPR1 and TGA2. Alternatively this weak interaction could be attributed to an endogenous level of SA. However a steady increase in fluorescence intensity is detected with increasing concentrations of SA. These results indicate that the SA-induced interaction of NPR1 with TGA2 can be monitored directly in plant cells using a PCA strategy. As shown in FIG. 7, after electroporation, various amounts of salicylic acid were added to protoplasts electroporated with either NPR1-F[1,2] alone or the two NPR-TGA constructs. The fluorometric readings obtained from the cells transformed with the single construct were subtracted from the reading obtained from the protoplasts transformed with both constructs. These relative fluorescence units (RFU) have been adjusted to both protein and GUS values. This is representative of at least five independent experiments and performed in triplicates.

Figure 8:
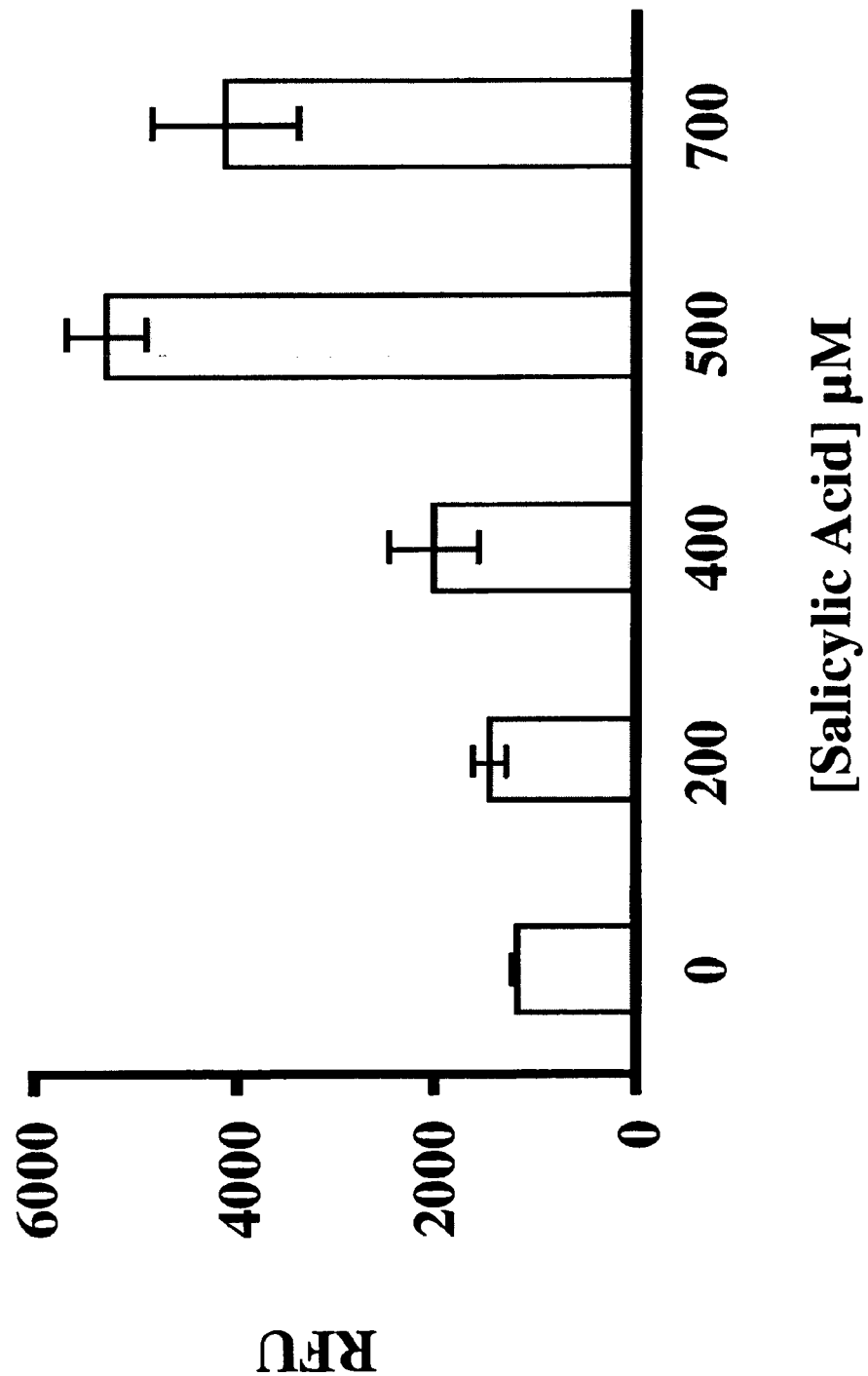
FIG. 8 illustrates the dose-response of NPR1-TGA2 in potato leaf protoplasts treated with SA.

Similar results were obtained with potato leaf protoplasts (FIG. 8), although in this case higher levels of SA were required to obtain the maximum signal. Theses results indicate that the PCA can be applied to different plant species. Also as further shown in FIG. 8, after electroporation, various amounts of SA were added to protoplasts electroporated with either NPR1-F[1,2] alone or the two NPR-TGA constructs. The fluorometric readings obtained from the cells transformed with the single construct were subtracted from the reading obtained from the protoplasts transformed with both constructs. These relative fluorescence units (RFU) have been adjusted to both protein and GUS values. This is representative of at least three independent experiments and performed in triplicates.

Figure 9:
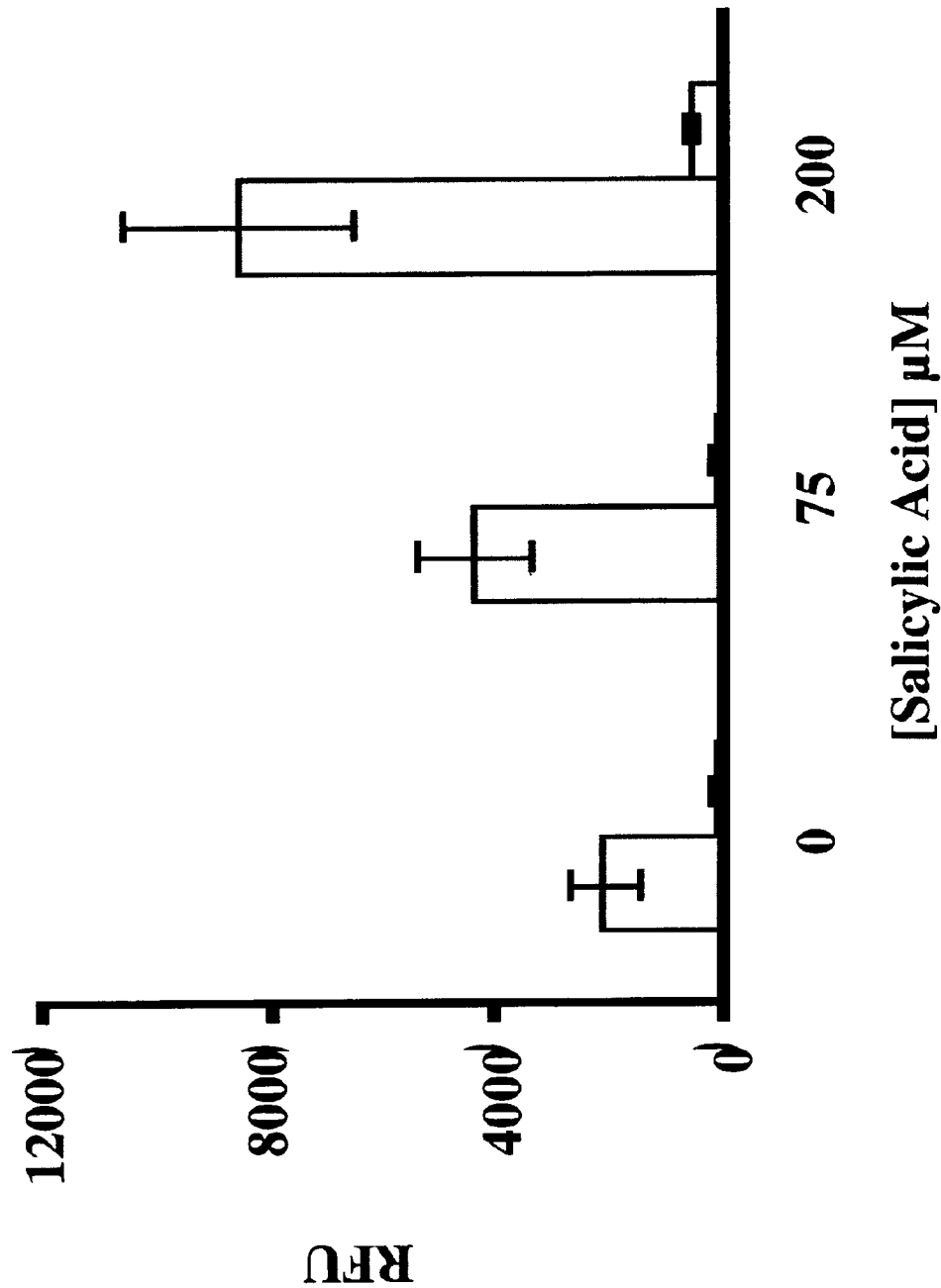
FIG. 9 describes that the npr1-1 mutant fails to interact with TGA2.

Additionally, to determine whether the interaction between NPR1 and TGA2 observed with the PCA is relevant to the biological function of NPR1 in plants, we tested the ability of the mutant protein npr1-1 to interact with TGA2. In Arabidopsis, this mutation (replacement of His-to-Tyr at position 334) leads to enhanced susceptibility to infection and the failure to mount an SAR.[25] As shown in FIG. 9, no significant signal was detected with the npr1-1 fusion protein, indicating that the SA-induced interaction detected between NPR1 and TGA2 with the PCA is biologically relevant. In the experiment summarized in FIG. 9, after electroporation, various amounts of SA were added to protoplasts electroporated with the NPR1/TGA2 or npr1-1/TGA2 constructs. The fluorometric readings obtained from the protoplasts transformed with a single plasmid (NPR1-DHFR or npr1-1-DHFR) have been subtracted from the readings obtained with cells transformed with two plasmids. These relative fluorescence units (RFU) have been adjusted to both protein and GUS values. This is representative of at least five independent experiments and performed in triplicates.

Figure 10:
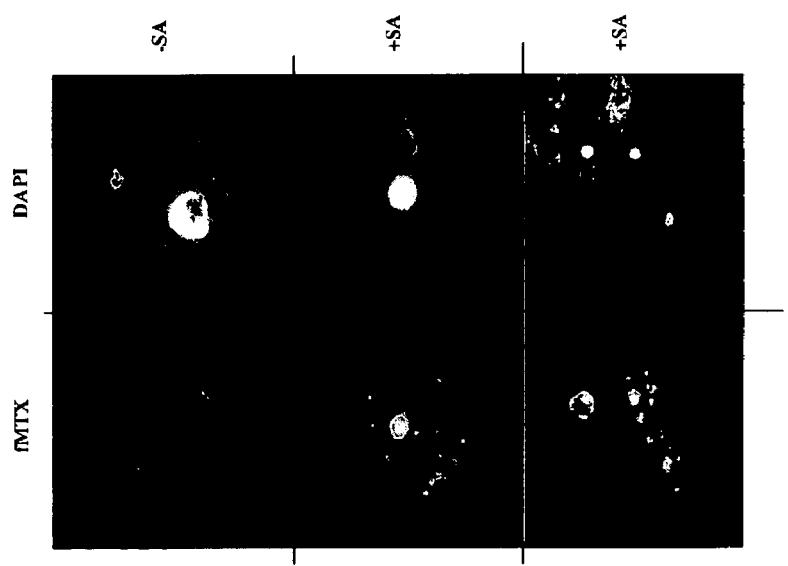
FIG. 10 describes the nuclear Localization of NPR1-TGA2 Interaction by Fluorescence Microscopy.

One of the strengths of the PCA strategy is its potential to detect protein-protein interactions in different cell compartments. This is now demonstrated in FIG. 10, where the interaction between NPR1 and TGA2 is shown to occur in the nuclei of transfected potato protoplasts. The nuclear localisation of the interaction is confirmed by double-staining of the protoplasts with the nuclear specific stain DAPI. In FIG. 10, the legends are as follows: A and B. Protoplasts transfected with NPR1-TGA2 fusion proteins and not treated with SA. C–F. Protoplasts transfected with NPR1-TGA2 fusion proteins and treated with SA. A, C and E. Fluorescein filter. B, D and F. UV filter.

Example 8
Detailed Approaches and Applications of the PCA Strategy to Plants

1) Transient expression in tissue explants. Plant protoplasts are fragile cells not always amenable to studies involving external stimuli. These cells have been subjected to harsh treatments including digestion with cellulases and hemicellulases and they do not respond to many inducing signals to which they would respond in an organized tissue. It would therefore be useful to develop a PCA system in whole tissues where cells are still able to respond to external stimuli. It should be possible to develop a rapid, transient assay system, and a system based on the expression of the mDHFR fusion proteins in transgenic plants.

The *Agrobacterium tumefasciens* leaf infiltration technique can be used. Vacuum infiltration of detached leaves with a culture of Agrobacterium containing foreign genes on a binary plasmid has been shown to lead to strong transient expression of the foreign genes in leaf tissue[28]. A similar technique, in which the bacteria are injected in leaf tissue instead of being infiltrated, has been used recently to show the interaction between the product of the bacterial avirulence gene avrPto and Pto, a protein kinase involved in the defense response[29].

Applicants' have developed a general method for the characterization of protein-protein interactions in intact leaves using the mDHFR PCA. The feasibility of this assay could be tested using the GCN4 leucine zippers-mDHFR fusion proteins used in the first part of this proposal. In this strategy, the two fusion proteins are transferred into the Ti binary plasmid pBTEX[29] that permits simultaneous expression of two genes, with each gene under the control of a separate CaMV 35S promoter. The recombinant plasmid is introduced into *Agrobacterium tumefasciens* strain EHA105 by electroporation. Leaves from in vitro grown potato plants are then vacuum infiltrated with this Agrobacterium. To assay for DHFR activity, leaves are placed in a solution containing fMTX and a mild vacuum is applied for 1 min, as described for the assay of β-glucuronidase with the substrate X-gluc in Agrobacterium-infiltrated leaves.[28] After 20 hrs, leaves are cleared in 95% ethanol to eliminate chlorophyll[30] and unbound substrate. Fluorescent cells are detected using a fluorescent dissection microscope equipped with a CCD video camera.

An alternative procedure is to select for stably transformed cells with methotrexate. As the reconstituted mDHFR enzyme that we used is resistant to methotrexate[14], only leaf cells that have integrated the Agrobacterium T-DNA will be able to grow in the presence of the drug. Transformed, green calluses should be detectable after 10 days of selection with methotrexate[31]. Then a few plants are regenerated from calluses and Southern blots are performed to confirm the integration of the DHFR constructs. Tissue explants can also be treated with fMTX and fluorescence monitored by microscopy to confirm the expression of the mDHFR fusion proteins. Control transformations are done with a Ti plasmid containing only one of the fusion proteins or only the mDHFR fragments.

2) Expression in transgenic plants. The PCA could be developed in transgenic plants. This would provide a useful system to study inducible interactions that occur only in a whole plant, as for the component of the systemic acquired resistance that occurs in distant leaves from the site of infection, and to study the effect of specific abiotic stresses on whole plants, such as cold or draught. We propose to use the model plant *Arabidopsis thaliana*, as the very large number of mutants available for this plant, and the fact that sequencing of its genome is completed, make it an ideal system to identify genes in pathways that are required for inducible interactions. Thus by using a specific mutant background to perform an inducible PCA assay, it would be possible to determine whether the mutated gene is acting upstream in the pathway controlling the inducible interaction, or controls a suppressor of the pathway. This technique could also be used to identify novel genes involved in such pathways by mutagenising seeds from transgenic plants expressing interacting partners. Mutagenized seeds would be germinated, treated with an inducer (e.g. a small molecule, an hormone, an abiotic stress or light) controlling the interaction of the two fusion proteins under study, and activity of the reporter enzyme monitored. Absent or reduced enzyme activity could indicate that a gene in the pathway being studied has been mutated. It would then be possible to clone the mutagenized gene, by map-based cloning if a chemical mutagenizing agent has been used, or by PCR if the mutation results from transposition of a transposable element after crossing with a line incorporating such an element.[32]

The ideal PCA for such a high-throughput screening procedure would be based on a reporter enzyme whose activity can be rapidly monitored, such as luciferase. Such PCAs are presently being developed in S. Michnick's laboratory (see below). In the mean time, the feasibility of the transgenic plant PCA approach could be demonstrated using the GCN4-mDHFR constructs and the NPR1/TGA2 inducible interaction. In the latter case, we could also attempt to select for mutants having lost the interaction between the two MTX-resistant mDHFR fusion proteins by sowing ethylmethane sulfonate mutagenized transgenic seeds[33] on low methotrexate-containing medium. Seeds showing retarded germination could be rescued by transfer on normal media containing a folate analog.[34]

The pBTEX Ti plasmid described in the previous section for the simultaneous expression of the two fusion proteins could be used for this study. Transgenic *Arabidopsis* plants are produced by the simplified in planta transformation protocol[35], which allows the production of a large number of transgenic seeds. Seeds are vapor-sterilized and grown on MS-Agar plates containing 50 μg/ml kanamycin. Leaves from growing plants are tested for survival on methotrexate-Agar plates and examined by the fMTX fluorescence assay. We can test the feasibility of rescuing seeds that have lost resistance to methotrexate by germinating a mixture of transgenic and non transgenic seeds in liquid medium containing low concentrations of methotrexate, followed by transfer of the non or slow germinating seeds in liquid or solid medium containing 5-formyl-tetrahydrofolate[34].

3) cDNA Screening Strategy for the Identification of Novel Interacting Proteins Using PCA Since its original description almost 10 years ago, the yeast two-hybrid system has been used extensively to identify protein-protein interactions from many different organisms. However, despite these successes, this system does not represent a universal system for gene discovery by protein-protein interactions. Developing experimental alternatives to this procedure represents a high priority. For example, there is a need to develop a system where putative interacting partners can be screened in cellular environments that are as close as possible to their normal environment. The PCA offers the possibility to develop such an approach in plant cells.

In the following sections we describe the vectors and constructions that could be used for the screening, and then we discuss the different strategies that would be tested to detect interacting partners.

a) Construction of the cDNA Library

The invention is also directed to the elucidation of the mechanisms that control the activation of specific genes during the defense response to pathogens in potato. We have now isolated a nuclear factor, PBF-2, containing a 30 kD protein (p30), that binds to a DNA element controlling the expression of the PR-10a defense gene of potato.[36] The DNA binding activity of this factor is regulated by a protein kinase C homolog and data suggest that protein-protein interactions may negatively regulate the activity of the factor[37]. We will construct a cDNA library in the vector pBI222 used to express the DHFR fusion proteins described in previous sections and use the p30 coding sequence as a bait to isolate putative interaction partners to this protein.

Applicants' can isolate poly(A)$^+$ RNA from tuber tissues that have been treated 3 hrs with an elicitor to induce the defense response. cDNA will be synthesized using the directional cDNA synthesis kit from Stratagene. The library will be constructed as a C-terminal fusion to mDHFR F[3] in vector pBI222, placing the fusion protein under the control of the CaMV 35S promoter. The cDNA fragments will be directionally inserted in the vector. Short oligonucleotides will be introduced in the vector to allow amplification by PCR of whole inserts, including the 35S promoter, for retesting clones that give a positive signal (see below). The p30 cDNA will be subcloned and inserted 3' to the mDHFR F[1,2] coding sequence in plasmid pBI222. This will put the fusion protein under the control of the 35S promoter.

b) Screening of the cDNA Library

To test the feasibility of screening a large number of genes with the PCA approach, we can first attempt a reconstruction experiment in which one of the clones encoding the GCN4 leucine zipper-mDHFR fusion protein described before is mixed at different dilutions with clones from the cDNA library. The bait vector contains the complementary GCN4 leucine zipper forming sequences-mDHFR fusion protein. This will show the feasibility of screening in plant cells large number of clones for the isolation of rare sequences with the PCA system. In CHO cells we have shown that individual clones can be detected when diluted in a background at 1 clone in $10^6$ [14].

Several approaches are feasible for the detection of protein-protein interactions and they include the following:

i) FACS. Detection of mDHFR activity is done by FACS, as this technique has many advantages, including speed, simplicity and sensitivity. However, the following alternative approaches could also be used.

ii) Video imaging and fluorescence measurements in microplates. Following electroporation, protoplasts are treated with fMTX as described above, washed, embedded in low melting agarose[38] and plated on Petri dishes. Fluorescent cells are detected using a fluorescent dissection microscope equipped with a CCD camera. Cells giving a positive signal are picked and plasmid inserts amplified by PCR using specific primers. Amplified fragments are cloned in the same vector, and a second round of screening is performed with protoplasts plated at a higher dilution.

As the imaging system may prove to be not sensitive enough to detect fluorescence in agarose-embedded single cells, we propose another alternative where electroporated protoplasts, incubated with fMET as above, are aliquoted into 384 wells microplates and fluorescence monitored using a microplate fluorimeter. Total DNA is isolated from protoplasts in wells giving a positive signal, the inserts amplified by PCR and subcloned in the mDHFR vector and the experiment repeated until a clonal population of fluorescent protoplasts is obtained. cDNA inserts from these cells can be reamplified as described above, cloned and sequenced.

iii) Particle bombardment. Bombardment by DNA-coated microparticles offers a convenient way to introduce and express a foreign gene in tissue explants[39]. Pools of plasmid DNA from the cDNA library is adsorbed on gold particles and introduced, using a helium-driven particle delivery system into detached potato leaves that have been vacuum-infiltrated with fMET. Leaves are processed as described in section 1.A and fluorescence detected using a dissection microscope. Pools giving a positive signal are detected and fractionated and the bombardment repeated. Alternatively, fluorescent spots can be excised from the leaf, the DNA extracted and amplified with the specific primers described in section B.1, and bombardment repeated until a single clone is isolated.

iv) Other approaches. It should be possible to use an autonomously replicating vector, such as PVX[40], to propagate the cDNA library into protoplasts after electroporation. This vector would only need to undergo a few rounds of replication, therefore permitting the selection of micro colonies from protoplasts that have been immobilized in agarose. Alternatively, a differential display[41] approach could be applied to the selection of cDNAs encoding interacting proteins if few rounds of DNA replication was achieved. Following electroporation, methotrexate would be added directly to the protoplasts in liquid culture. After 5–10 days, DNA would be extracted from these cells and cDNAs in the vector amplified by PCR using the primers specific for the library vector. By comparing on a high resolution gel the pattern of amplified fragments with that obtained using control cells electroporated with the cDNA library and the vector carrying only the mDHFR fragment (without the bait protein), it should be possible to detect fragments that are more abundant due to the selective replication of the corresponding cDNAs in protoplasts in the presence of methotrexate. These fragments would then be reamplified, cloned, analyzed by restriction enzyme fingerprinting and sequenced.

Finally, Applicant is also developing other PCAs in which a fluorescent product is produced from reconstitution of an enzyme, including assays based on β-lactamase and firefly and renilla luciferase. These assays may prove useful to the long term objectives of this project and as alternative approaches to the DHFR assays.

IV. Application of the PCA to Plants and Agriculture

The invention has broad applications of the PCA strategy to plant biology and agriculture. They include the following:

A. Gene Delivery.

The gene delivery system can be electroporation of plasmids containing the PCA fragments; PEG or any chemical mean of transformation, *Agrobacterium tumefasciens* or any other bacteria; particle bombardment; etc.

The PCA fragments can be inserted into a vector able to autoreplicate in plant cells, such as a vector derived from a plant virus (ex. PVX). This could be an autonomously replicating artificial chromosome.

The two PCA fragments can be introduced in separate cells that are then fused to produce single cells harboring the two fragments. Transgenic plants containing the individual fragments can also be mated such that the progeny contains the two PCA fragments.

B. Detection of Inducible and Non-Inducible Protein-Protein Interactions in Plant Cells.

One can determine whether two proteins interact together and characterize the structural requirements for this interaction (e.g. protein domains and specific amino acids).

This interaction can be detected and analyzed in appropriate contexts, such as within a specific species, cell type, cellular compartment, or organelle.

The interaction could be monitored in isolated cells, such as protoplasts and cell suspension cultures, and in organized tissues, grown in vitro or not, such as a callus, a tissue explant (ex. detached roots, leaves, flowers, pollen, fruit, stem, etc.) and in whole plant (any plant species).

The interaction can be monitored in transient expression assays or in stably transformed cells and whole plants.

The interaction could be monitored extracellularly, such as in intercellular spaces in differentiated plant tissues.

The interaction could be monitored in isolated organelles, such as in nuclei, chloroplasts and other plastids, in mitochondria, vacuoles, etc.

The interaction can be studied whether it occurs constitutively or only in the presence of an inducing factor.

Examples of inducing factors include environmental factors such as light, cold, draught, water, air pollution, wind, rain, wounding, pest and pathogens, deficient soils (ex. salinity, high aluminum levels, extreme pH, nitrogen and other nutrient imbalances), developmental signals and signals linked to fertilization, hormonal signals, chemical signals (ex. pesticides, herbicides, bioregulators, etc.), etc.

The kinetic and equilibrium aspects of protein assembly in plant cells can be determined by the PCA, including effect of small molecules on these parameters.

The PCA could be coupled to a mutagenesis approach to identify genes controlling the interaction between protein partners.

C. Screening of Gene Libraries for the Identification of Novel Interacting Proteins.

The PCA could be used to identify genes encoding proteins able to interact with a bait protein expressed in a plant cell.

The technique could be used to identify proteins that interact only in specific plant organelles or cell compartments.

The technique would allow the identification of gene products that interact only in biochemical pathways specific to plants.

The screen can be performed in transient expression assays in plant protoplasts, in cell suspension culture, in tissue explants, in plant organs or in whole plants.

The gene delivery system can be as described in IV-A.

D. High Throughput Screening (HTS) for Small Molecules (Including Peptides, Lipids and Polysaccharides) Affecting the Interaction between Two Proteins.

When the interaction of two proteins is involved in the control of a physiological, pathological or developmental processes in plants, it becomes possible to screen for small molecules able to modulate the interaction of these proteins and thus able to affect these processes. These small molecules can inhibit or stimulate the protein-protein interaction by interacting directly with one or both protein partners, or it can interact with another molecule involved in the pathway regulating the interaction between the protein partners.

The screening can be performed with any plant material as long as protein-protein interactions can be monitored by the PCA. This includes protoplasts, cell suspension culture, callus, tissue explants, pollen grain, plant organs, whole plant.

The screening can be done with stably transformed cells, tissues or whole plants, or with cells that transiently express the reporter genes (see section II).

One can screen for molecules that induce or inhibit the interaction.

Examples of processes important in agriculture where this HTS could be applied: Screening for small molecules (bioregulators) affecting the control of rooting and propagation; that can promote, delay or prevent flowering; control fruit set and development; control sex on plants; control plant or organ size and physiognomy; induce or prevent abscission (the falling off of leaves and fruit); control senescence or maturity; regulate metabolic processes; acting as gametocides, overcoming environmental stresses (see section II); control of germination and dormancy; increasing resistance to pests and pathogens; maintenance of fruit firmness in storage after harvest; prevention of post-harvest spoilage; changing the chemical composition of plant or plant parts; control of color; influence mineral uptake from the soil; protection against herbicidal damage; acting as adjuvents to herbicides to increase their activity; as herbicide; to control the timing of crop development; etc.

Example of Targets:

Pto and Pti1: It has been shown that the product of these genes interacts during the defense response. It could therefore be possible to screen for small molecules able to induce this interaction. This would allow identification of a bioregulator inducing natural defense in plants. This strategy could be repeated anytime a R gene product (gene conferring resistance to a pathogen) is known to interact with another protein after induction of the defense response. But the gene does not need to be an R gene, as long as it is in the signaling pathway leading to the defense response. An example of this is the systemic acquired resistance (SAR) in plants described before. The PCA described in the present application where SA induces the interaction between NPR1 and TGA2 could be used to screen for molecules more potent than SA for the induction of the SAR. These molecules then could be used as inducers of natural resistance in the field.

Herbicides: Genetic evidences indicate that the products of the *Arabidopsis clavata* 3 and *clavata* 1 gene interacts and that this interaction is required for stem meristem formation. If such an interaction could be demonstrated in a plant PCA system, this could form the basis for an HTS for molecules acting as herbicide. This strategy could be used to isolate molecules interfering with the assembly of rubisco (small and large subunits) or any other interacting proteins known to be involved in photosynthesis.

Engineering plants with mutants of interacting proteins:

a) Once small molecules have been found (using the PCA or any other approach) that are able to modulate (inhibit or induce) the interaction between two proteins, thus leading to the modification of physiological or developmental process (or any useful phenotype), then the PCA can be used to isolate mutants of the interacting proteins that are not sensitive anymore to the small molecule. For example, random mutations can be introduced in the gene of one of the interactors and the effect of each mutation tested with the PCA in presence of the small molecule affecting the interaction. One then select for mutations that suppress the effect of the small molecule. The mutant gene can then be used to make transgenic plants that are resistant to the small molecule. Example of applications could be:

b) Herbicide resistance: An herbicide that leads to the disruption of a protein-protein interaction vital for the survival of the plant is used to select, by the PCA (as described above), mutations in one of the interacting partner that renders the interaction insensitive to the effect of the herbicide. The mutated gene is then introduced into a crop plant. Weeds can then be controlled by application of the herbicide, without fear for the crop, thus allowing a limited use of herbicides for the control of weeds.

c) Control of flowering: When the interaction between two proteins is known to control flowering, the PCA can be used to isolate a small molecule that disrupt this interaction. This molecule can then be used to retard flowering, which might be useful, especially for production of ornamental plants, and for crop plants where this could allow the plant to increase its bio mass before harvesting. The same can be done for the isolation of small molecules that would induce flower development by inducing the interaction of two proteins. Then the small molecule could be used to obtain early flowering. This could have some applications for example in crops grown in colder climates where it can be useful to induce flowering before early frosts destroy the crop.

d) Production of hybrid plants: Hybrid plants are largely used in agriculture (ex. maize) as these plants usually show increased vigor and other enhanced characteristics. These plants are normally produced using male sterile plants, such that female flowers on a plant can only be fertilized by the pollen of another species, leading to the production of hybrid seeds. However, a way must be provided to restore the fertility of the male sterile plant, such that seeds for these plants can be obtained. When two interactors are known to be required for the production of male gametes, it is possible to use the PCA (or any other methods) to select for small molecules that disrupt this interaction. It is then possible to treat the plants with this small molecule to inhibit male flower development, such that these plants can only be fertilized by non-treated plants, thus allowing the production of hybrid seeds. Progenitor seeds are produced from untreated plants.

A similar mutagenesis strategy coupled to the PCA could be used to isolate genes encoding for proteins resistant to the action of a small molecule. This would be especially useful when the target protein does not have intrinsic activity easily measurable in vitro. An example would be a protein that controls directly, or indirectly, the interaction between two proteins. Mutant proteins that are not sensitive to inhibition by the small molecule could be isolated by the PCA. The genes could then be used to produce transgenic plants resistant to the small molecule.

The PCA could be used to identify new intermediates in signal transduction pathways. For example, using the salicylic acid inducible NPR1-TGA2 PCA system described in the present application: protoplasts would be cotransfected with the NPR1 and TGA2 DHFR plasmids, and with a plant cDNA expression library. Overexpression of a cDNA encoding a protein in the NPR1/TGA2 pathway could lead to activation of the pathway, and thus of the interaction between NPR1 and TGA2, even in the absence of SA. The fluorescence assay would allow the isolation of the protoplast(s) transformed with such cDNAs, and thus isolation of the cDNA by PCR.

e) Use of the cosuppression approach to isolate genes involved in signal transduction pathway. A cDNA expression library, under the expression of a constitutive plant promoter, is constructed into a viral vector derived form PVX. The vector is inserted into the tDNA region of *Agrobacterium tumefasciens* and colonies are isolated. When leaves of a plant, for example *Nicotiana benthamiana* are infiltrated with a culture from a single colony, the cDNA is integrated into the plant genome, and its expression leads to cosuppression of the gene homologous to the sequence of the cDNA. If this gene is important for a pathway, this can be detected by inducing the pathway (for ex. resistance to a pathogen and scoring for infection; infection of individual plants with a few thousand colonies leads to the identification of signal transduction intermediates). This technique, developed by David Baulcombe and collaborators, is limited by the phenotypes that can be observed. We propose to link this technique to the PCA for the detection of signal transduction intermediates: transgenic plants coexpressing two interacting proteins linked to a reporter fragment would be produced. These plants would then be agro-infiltrated and fluorescence measured after treatment with fMTX of co-suppressed leaves. Reduction of fluorescence would indicate that a gene in the pathway has been repressed. The repressor cDNA could easily be isolated by PCR. This would allow isolation of genes for pathways where no obvious phenotypes are detectable.

References.

1. Aruffo, A. & Seed, B., 1987. *Proc. Natl. Acad. Sci.* USA 84: 8573–7.
2. D'Andrea, A. D. et al., 1989. *Cell* 57: 277–285.
3. Lin, H. Y. et al., 1992. *Cell* 68: 775–85.

4. Sako, D. et al., 1993. *Cell* 75: 1179–86.
5. Evangelista, C. et al., 1996. *Trends in Cell Biology* 6: 196–199.
6. Fields, S. & Song, O., 1989. *Nature* 340: 245–6.
7. Drees, B. L., 1999. *Curr Opin Chem Biol* 3: 64–70.
8. Vidal, M. & Legrain, P., 1999. *Nucleic Acids Res* 27: 919–29.
9. Michnick, S. W. et al., in *Methods in Enzymology* (eds. Abelson, J. N., Emr, S. D. & Thorner, J.) (Academic Press, New York, 1999).
10. Pelletier, J. N., Arndt, K. M., Plückthun, A. & Michnick, S. W., 1999. *Nature Biotechnology* 17: 683–690.
11. Pelletier, J. N., Campbell-Valois, F. & Michnick, S. W., 1998. *Proc Natl Acad Sci USA* 95: 12141–6.
12. Pelletier, J. N., I. Remy and S. W. Michnick., 1998. *J. Biomolec. Techn.* accession number S0012.
13. Remy, I., I. A. Wilson, and S. W. Michnick, 1999. *Science* 283: 990–993.
14. Remy, I. & Michnick, S. W., 1999. *Proc Natl Acad Sci USA* 96: 5394–5399.
15. Livnah, O. et al., 1999. *Science* 283:
16. Chen, J. et al., 1995. *Proc Natl Acad Sci USA* 92: 4947–51.
17. Cao, H. et al., 1997. *Cell* 88: 57–65.
18. Magnien, E., et al., 1980. *Plants Sci. Letters* 19: 231–241.
19. Matton, D. P. et al., 1993 *Plant Mol. Biol.* 22, 279–291.
20. Jefferson R. A, et al., 1987. *EMBO J* 6: 3901–3907.
23. Uknes, S. et al., 1992. Plant Cell 4: 645–656. 26.
24. Ryals, J. A. et al., 1997. *Plant Cell* 9: 425–439.
25. Zhang, Y. et al., 1999. *Proc. Natnl. Acad. Sci. USA* 96: 6523–6528.
26. Després, C., et al., 2000. *Plant Cell* 12, 279–290.
27. Zhou, J.-M. et al., 2000. *Molec. Plant Microbe Interact.*
28. 13:191–202. 28. Kapila, J. et al., 1997. *Plant Science* 101–108.
29. Frederick, R. D. et al., 1998. *Molec. Cell* 2: 242–245.
30. Constabel, C. P. and Brisson, N. 1995. *Molec. Plant-Microbe Interac.* 8: 104–113.
31. Irdani, T. et al., 1998. *Planta* 37: 1079–1084.
32. http://genome-www.stanford.edu/Arabidopsis/cshl-course/.
33. http://www.cnrs-gif.fr/isv/EMBO/manuals/.
34. Prabhu V. et al., 1998. *Plant Physiology.* 116:137–144.
35. Clough, S. J. and Bent A. F. 1998. *Plant J.* 16:735–743.
36. Després, C. et al., 1995. *Plant Cell* 7: 589–598.
37. Subramaniam, R., Després, C. and Brisson, N. 1997. Plant Cell 9: 653–664.
38. Bengochea, T. and Dodds, J. H. 1986. Plant Protoplasts. Chapman & Hall (New York) 90p.
39. Christou, P., 1992. *Plant J.* 2: 275–281.
40. Chapman S., et al., 1992. *Plant J.* 2:549–557.
41. Liang, P. et al., 1993. *Nuc. Acids Res.* 21: 3269–3275.

Although the present invention has been described with reference to specific details of certain embodiments thereof, it is not intended that such detail should be regarded as limitations upon the scope of the invention, except as and to the extent that they are included in the accompanying claims.

What is being claimed is:

1. A method of expressing PCA (protein fragment complementation assays) interacting protein partners in plant material comprising:
  (A) transforming said plant material with:
    (1) a first PCA interacting protein partner construct coding for a first fusion product comprising:
      (a) a first fragment of a dihydrofolate reductase enzyme which fragment associates with a second fragment of said dihydrofolate reductase enzyme to produce a detectable enzymatic activity and
      (b) a first protein-protein interacting domain; and
    (2) a second PCA interacting protein partner construct coding for a second fusion product comprising:
      (a) a second fragment of said dihydrofolate reductase enzyme and
      (b) a second protein-protein interacting domain that can bind said first protein-protein interacting domain;
  (B) culturing said material under conditions allowing expression of said PCA interacting protein partners, and allowing interaction of said first protein-protein interacting domain with said second protein-protein interacting domain;
  (C) directly or indirectly testing for reconstitution of said enzymatic activity when said dihydrofolate reductase enzyme fragments are associated.

* * * * *